(12) United States Patent
Suzuki et al.

(10) Patent No.: US 6,171,595 B1
(45) Date of Patent: Jan. 9, 2001

(54) SKIN EXTERNAL PREPARATION

(75) Inventors: Yasuto Suzuki; Naoko Tsuji; Shigeru Moriwaki; Yoshinori Nishizawa; Yoshinori Takema; Satoshi Kanazawa; Genji Imokawa; Yukihiro Ohashi; Mikako Watanabe, all of Haga-gun (JP)

(73) Assignee: Kao Corporation, Tokyo (JP)

( * ) Notice: Under 35 U.S.C. 154(b), the term of this patent shall be extended for 0 days.

(21) Appl. No.: 09/480,794

(22) Filed: Jan. 11, 2000

Related U.S. Application Data

(62) Division of application No. 09/276,504, filed on Mar. 25, 1999, now Pat. No. 6,075,052.

(30) Foreign Application Priority Data

Mar. 27, 1998 (JP) .................................. 10-081418

(51) Int. Cl.[7] ................................. A61K 39/385
(52) U.S. Cl. ........................................ 424/195.1
(58) Field of Search .................... 514/880; 424/195.1

(56) References Cited

U.S. PATENT DOCUMENTS

| 5,196,534 | 3/1993 | Whitehead et al. . |
| 5,217,994 | 6/1993 | Egbertson et al. . |
| 5,294,616 | 3/1994 | Duggan et al. . |
| 5,391,466 | 2/1995 | Ueda et al. . |
| 5,750,702 | 5/1998 | Albaugh et al. . |
| 5,766,633 | 6/1998 | Milstein et al. . |

FOREIGN PATENT DOCUMENTS

| 18199 | * 10/1980 | (EP) . |
| 10-17460 | 1/1998 | (JP) . |
| 10265347 | * 10/1999 | (JP) . |
| WO 98/25580 | 6/1998 | (WO) . |

OTHER PUBLICATIONS

Yasunori et al, hair–restoring or growing accelerator, patent abstracts of Japan: JP 01246211, 1989, vol. 13(589), p. 6.*
Ueno et al , Hair growth stimulant, patent abstract of Japan :JP11310518, 1999.*

* cited by examiner

*Primary Examiner*—William R. A. Jarvis
*Assistant Examiner*—Vickie Kim
(74) *Attorney, Agent, or Firm*—Oblon, Spivak, McClelland, Maier & Neustadt, P.C.

(57) ABSTRACT

The present invention provides a skin external preparation comprising a compound of the formula (1), (2), (3) or (4).

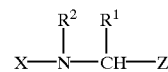

(1)

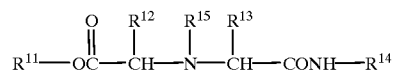

(2)

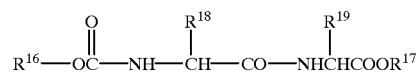

(3)

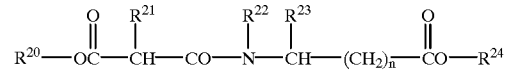

(4)

wherein X represents COOH, etc., Z represents $CONH_2$, etc. and $R^1$ and $R^7$ individually represent a hydrogen atom, etc.

The above-described compound has excellent effects, for example, for preventing or alleviating skin aging or inhibiting hair growth.

4 Claims, No Drawings

SKIN EXTERNAL PREPARATION

This application is a Division of application Ser. No. 09/276,504 filed on Mar. 25, 1999, now U.S. Pat. No. 6,075,052.

BACKGROUND OF THE INVENTION

1. Field of the Invention

The present invention relates to a skin external preparation having effects for preventing or alleviating skin aging or for inhibiting hair growth.

2. Description of the Related Art

As a result of researches on the aging of the skin, influences of aging, drying, oxidation, sun light (ultraviolet ray) and the like are mentioned as the causes for the aging of the skin. The aging of the skin is recognized by a decrease of collagen or elastin in the dermis of the skin, a decrease in mucopolysaccharides including hyaluronic acid, cellular damage by ultraviolet rays or the like.

For the prevention of wrinkle formation, however, sufficient effects have not yet been attained, for example, by a collagen-containing cosmetic composition. In addition, various researches have been made on the aging of the skin caused by exposure to ultraviolet rays in consideration of the relation with ultraviolet rays, however, a cosmetic composition superseding an ultraviolet absorber or ultraviolet protector has not yet been developed.

There is an increasing tendency to have a liking for a hairless body, particularly, hairless arms or legs, from the viewpoint of aesthetic appearance. In order to remove the body hair, various methods have been made use of, for example, a mechanical removing method by using a shaver, a pair of hair-tweezers or the like, a method of removing the hair even from the hair bulb by using a depilatory agent and a method of removing the body hair by the chemical action of a depilatory agent.

The above-described hair removing methods however give physical or chemical stimulation to the skin and in addition, are limited in maintaining the removed state. There is accordingly a demand for the development of a method which facilitates the body hair removal.

SUMMARY OF THE INVENTION

An object of the present invention is to provide a skin external preparation having effects for preventing or alleviating the aging of the skin such as formation of wrinkles or for inhibiting hair growth.

The present invention relates to a skin external preparation comprising a compound represented by any one of the following formulas (1), (2), (3) and (4):

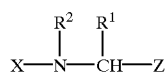
(1)

wherein X represents

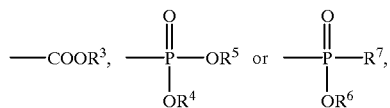

Z represents —CON($R^8$)$R^9$ or —COO$R^{10}$, $R^1$ represents a hydrogen atom or a substituted or unsubstituted alkyl, alkenyl, aralkyl or alkoxy group, or with $R^2$, may form a heterocyclic ring together with the adjacent nitrogen atom, $R^2$ represents a hydrogen atom or a $C_{1-6}$ alkyl or alkenyl group, or with $R^1$, may form said heterocyclic ring, $R^3$, $R^8$, $R^9$ and $R^{10}$ individually represent a hydrogen atom, an alkyl group or an alkenyl group, $R^4$, $R^5$ and $R^6$ individually represents a hydrogen atom, an alkyl group, an alkenyl group or an aralkyl group, and $R^7$ represents an aralkyl group;

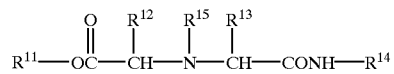
(2)

wherein $R^{11}$ represents a hydrogen atom or a $C_{1-12}$ alkyl or alkenyl group, $R^{12}$ and $R^{14}$ individually represent a hydrogen atom or a $C_{1-8}$ alkyl group, $R^{13}$ represents a hydrogen atom or a substituted or unsubstituted alkyl, alkenyl or aralkyl group, or with $R^{15}$, may form a heterocyclic ring together with the adjacent nitrogen atom, and $R^{15}$ represents a hydrogen atom or with $R^{13}$, may form said heterocyclic ring;

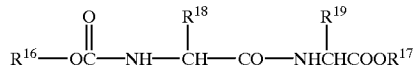
(3)

wherein $R^{16}$ and $R^{17}$ individually represent a hydrogen atom or an alkyl or alkenyl group, and $R^{18}$ and $R^{19}$ individually represent a hydrogen atom, an aralkyl group or a substituted or unsubstituted alkyl or alkenyl group;

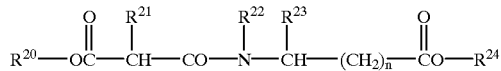
(4)

wherein $R^{20}$ represents a hydrogen atom, a $C_{1-8}$ alkyl or alkenyl group or an aralkyl group, $R^{21}$ represents a hydrogen atom or a substituted or unsubstituted alkyl, alkenyl or aralkyl group, $R^{22}$ represents a hydrogen atom or a $C_{1-6}$ alkyl or alkenyl group, or with $R^{23}$, may form a heterocyclic ring with the adjacent nitrogen atom, $R^{23}$ represents a hydrogen atom or a substituted or unsubstituted alkyl, alkenyl or aralkyl group, or with $R^{22}$, may form said heterocyclic ring, $R^{24}$ represents a hydrogen atom or a $C_{1-8}$ alkyl or alkenyl group, and n stands for an integer of 0 to 5.

In the above formula (2), the compound represented by the following formula (2a):

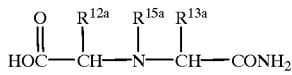

wherein $R^{12a}$ represents a hydrogen atom or a $C_{1-8}$ alkyl group, $R^{13a}$ represents a hydrogen atom or an alkyl or aralkyl group which may be substituted by a carbamoyl group, $R^{15a}$ represents a hydrogen atom or with $R^{13a}$, may form a pyrrolidinyl or piperidinyl group together with the adjacent nitrogen atom; or a salt thereof is novel and the present invention also provides this compound or salt thereof.

The skin external preparation according to the present invention has excellent effects for preventing or alleviating the aging of the skin or for inhibiting hair growth and can be synthesized easily.

DETAILED DESCRIPTION OF THE PREFERRED EMBODIMENTS

A description will next be made of the compound of the formula (1).

In the formula (1), $R^1$ preferably represents a hydrogen atom, a $C_{1-12}$ alkyl or alkenyl group which may have a substituent, a $C_{7-16}$ aralkyl group or a $C_{1-12}$ alkoxy group. As the alkyl or alkenyl group which may have a substituent, a linear or branched $C_{1-12}$ alkyl or alkenyl group, and a $C_{1-6}$ alkyl or alkenyl group having a substituent such as carbamoyl, hydroxy or carboxyl group are more preferred, of which linear or branched $C_{3-5}$ alkyl or alkenyl groups and $C_{1-4}$ alkyl or alkenyl groups having the above-described substituent are still more preferred. Among them, preferred examples include n-propyl, isopropyl, isobutyl, sec-butyl, tert-butyl, carbamoylmethyl, 2-carbamoylethyl and hydroxymethyl groups. Examples of the aralkyl group include phenylalkyl and naphthylalkyl groups, of which phenyl-$C_{1-6}$ alkyl groups are preferred, with benzyl and phenetyl groups being more preferred. As the alkoxy group, linear or branched $C_{1-8}$ alkoxy groups are preferred.

X represents —COOR$^3$,

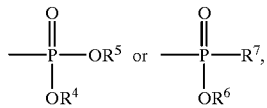

with the —COOR being preferred. As $R^3$, a hydrogen atom and $C_{1-12}$ alkyl or alkenyl groups are preferred, with a hydrogen atom, and methyl, ethyl, n-propyl, n-butyl and isobutyl groups are particularly preferred. As each of $R^4$, $R^5$ and $R^6$, a hydrogen atom, $C_{1-6}$ alkyl or alkenyl groups and $C_{7-16}$ alkyl groups are preferred, with a hydrogen atom and methyl, ethyl and benzyl groups being particularly preferred. As $R^7$, $C_{7-16}$ aralkyl groups are preferred, with benzyl and phenethyl groups being particularly preferred.

$R^2$ is preferred when it represents a hydrogen atom or a $C_{1-6}$ alkyl or alkenyl group, or it is coupled with $R^1$ to form a pyrrolidine ring. Z represents —CON($R^8$)$R^9$ or —COOR$^{10}$, with the —CON($R^8$)$R^9$ being preferred. As each of $R^8$, $R^9$ and $R^{10}$, a hydrogen atom and $C_{1-6}$ alkyl or alkenyl groups are preferred, with a hydrogen atom being more preferred.

A description will next be made of the compound of the formula (2).

In the formula (2), as $R^{11}$, a hydrogen atom and $C_{1-6}$ alkyl groups are preferred, with a hydrogen atom and methyl, ethyl, n-propyl, isopropyl, n-butyl and isobutyl groups being particularly preferred. As each of $R^{12}$ and $R^{14}$, a hydrogen atom and $C_{1-6}$ alkyl groups are preferred, with a hydrogen atom and methyl group being particularly preferred. As $R^{14}$, the hydrogen atom is particularly preferred. As $R^{13}$, a hydrogen atom, $C_{1-6}$ alkyl or alkenyl groups each of which may be substituted with a carbamoyl group and $C_{7-16}$ aralkyl groups are preferred, with a hydrogen atom, $C_{1-4}$ alkyl or alkenyl groups each of which may be substituted with a carbamoyl group and phenyl-$C_{1-6}$ alkyl groups being more preferred and isopropyl, isobutyl, sec-butyl, benzyl and 2-(carbamoyl)ethyl groups being particularly preferred. $R^{15}$ is particularly preferred when it represents a hydrogen atom or with $R^{13}$, forms a pyrrolidinyl or piperidinyl group together with the adjacent nitrogen atom.

A description will next be made of the compound of the formula (3).

In the formula (3), as each of $R^{16}$ and $R^{17}$, a hydrogen atom and $C_{1-6}$ alkyl or alkenyl groups are preferred, with a hydrogen atom and methyl, n-propyl, isopropyl, n-butyl and isobutyl groups being particularly preferred. Preferred examples of each of $R^{18}$ and $R^{19}$ include a hydrogen atom, phenylalkyl groups (particularly, phenyl-$C_{1-6}$ alkyl groups), naphthylalkyl groups (particularly, naphthyl-$C_{1-6}$ alkyl groups) and $C_{1-5}$ alkyl or alkenyl groups each of which may be substituted with a hydroxyl, methylthio, amino or 3-indolyl groups. Among them, the hydrogen atom and benzyl, isopropyl, isobutyl, sec-butyl, 1-hydroxyethyl, 2-(methylthio)ethyl group, 4-aminobutyl group and 3-indolylmethyl groups are particularly preferred.

A description will next be made of the compound of the formula (4).

In the formula (4), as $R^{20}$, a hydrogen atom, $C_{1-4}$ alkyl or alkenyl groups and aralkyl groups are preferred, with a hydrogen atom and methyl, ethyl, n-propyl, isopropyl, n-butyl and isobutyl groups are particularly preferred. Examples of the aralkyl group include phenylalkyl, biphenylalkyl and naphthylalkyl groups, of which phenyl-$C_{1-6}$ alkyl and biphenyl-$C_{1-6}$ alkyl groups are preferred, with benzyl and 4-phenylbenzyl groups being more preferred.

As $R^{22}$, a hydrogen atom is most preferred.

As each of $R^{21}$ and $R^{23}$, a hydrogen atom, linear or branched $C_{1-12}$ alkyl or alkenyl groups and aralkyl groups are preferred, of which a hydrogen atom, linear or branched $C_{3-6}$ alkyl or alkenyl groups are more preferred, with a hydrogen atom and n-propyl, isopropyl, isobutyl, sec-butyl and tert-butyl groups being particularly preferred. Examples of the aralkyl group include phenylalkyl and naphthylalkyl groups, of which phenyl-$C_{1-6}$ alkyl groups are preferred, with benzyl and phenethyl groups are still more preferred.

As $R^{24}$, a hydrogen atom and $C_{1-4}$ alkyl or alkenyl groups are preferred, with a hydrogen atom and methyl, ethyl, n-propyl, isopropyl, n-butyl and isobutyl groups being particularly preferred.

As n, 0 or 1 is most preferred.

Examples of the salt of each of the compounds (1), (2), (3) and (4) include alkali metal salts, alkaline earth metal salts, amine salts, amino acid salts and acid addition salts, of which alkali metal salts and amino acid salts are preferred. The compound of each of the formulas (1) to (4) may have optical activity and its steric configuration may be any one of R, S and racemic forms. The compound may also be in the form of a hydrate.
Among the compounds of the formula (1), the following compounds are particularly preferred.
(Compound 1-5)
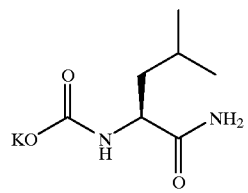
(Compound 1-8)
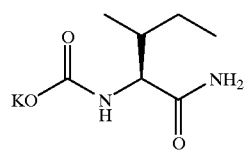
(Compound 1-15)
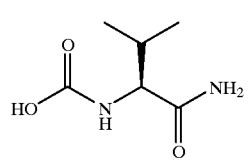
(Compound 1-7)
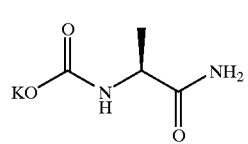
(Compound 1-2)
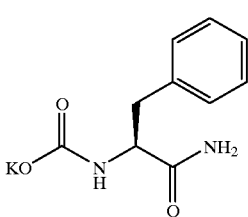
(Compound 1-14)
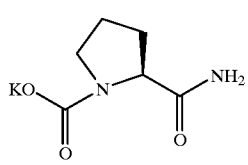
(Compound 1-13)
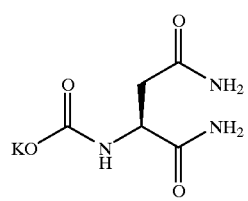
(Compound 1-16)
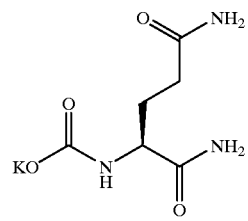
(Compound 1-17)
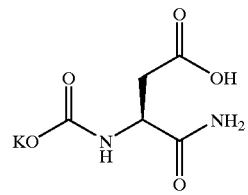
(Compound 1-18)
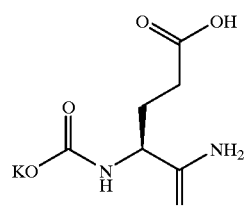
(Compound 1-19)
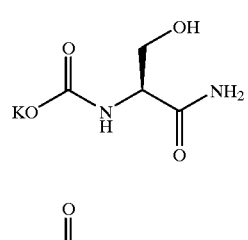
(Compound 1-11)
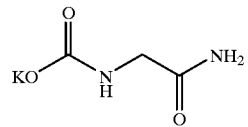
(Compound 1-1)
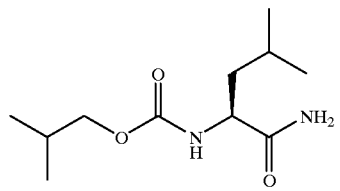
(Compound 1-9)
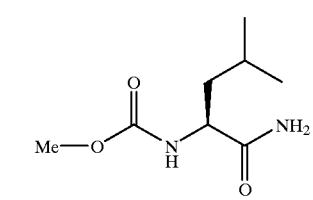
(Compound 1-20)
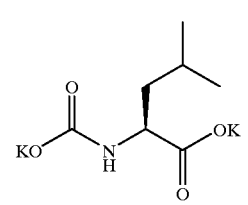

(Compound 1-6)
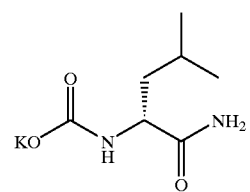
(Compound 1-4)
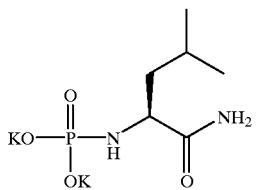
(Compound 1-10)
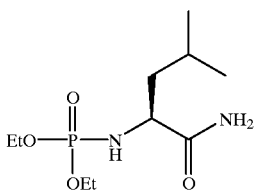
(Compound 1-3)
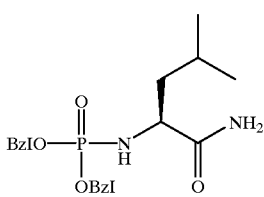
(Compound 1-21)
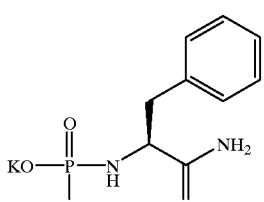
(Compound 1-12)
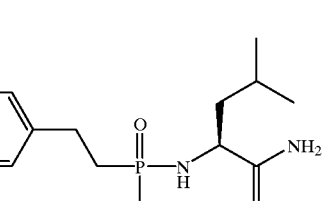
Among the compounds of the formula (2), the following compounds are particularly preferred.
(Compound 2-1)
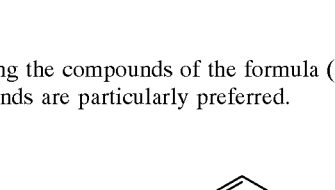
(Compound 2-2)
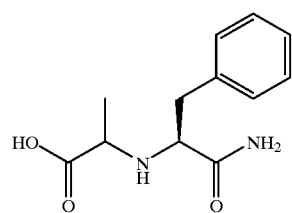
(Compound 2-3)
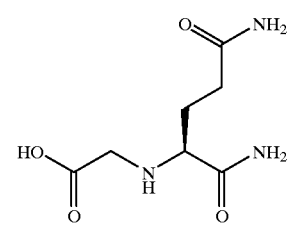
(Compound 2-4)
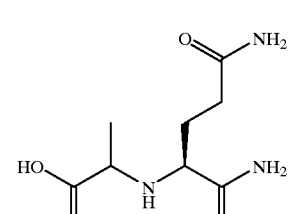
(Compound 2-5)
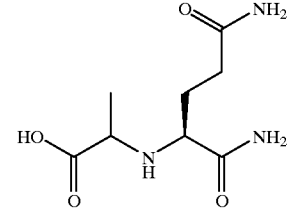
(Compound 2-6)
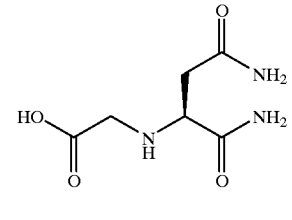
(Compound 2-7)
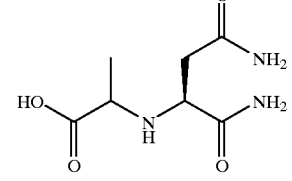
(Compound 2-8)
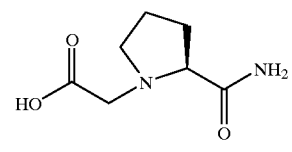

(Compound 2-9)

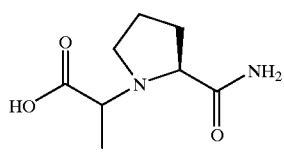

Among the compounds of the formula (3), the following compounds are particularly preferred.

(Compound 3-1)

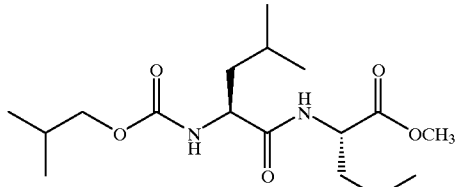

(Compound 3-2)

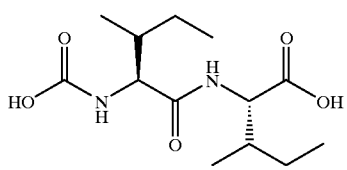

(Compound 3-3)

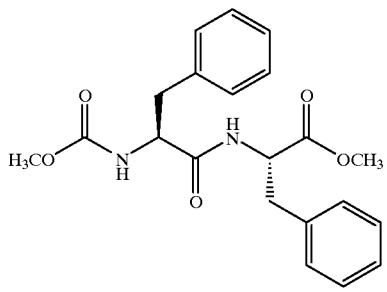

(Compound 3-4)

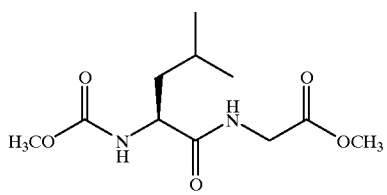

(Compound 3-5)

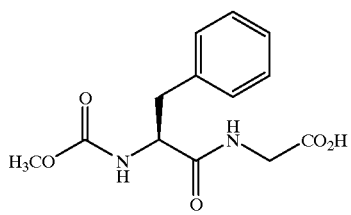

Among the compounds of the formula (4), the following compounds are particularly preferred.

(Compound 4-1)

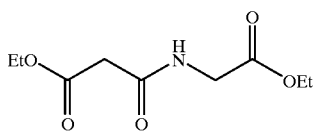

(Compound 4-2)

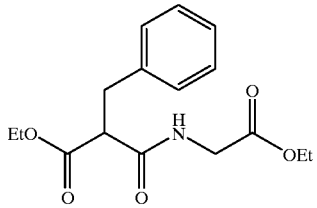

(Compound 4-3)

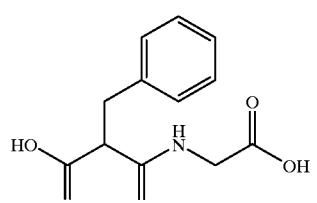

(Compound 4-4)

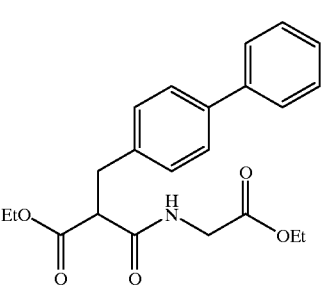

(Compound 4-5)

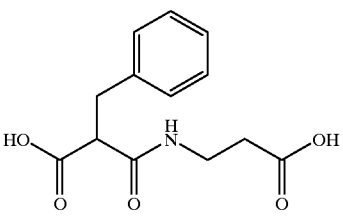

(Compound 4-6)

Each of the compounds of the formula (1) can be prepared, for example, in accordance with the procedure described in Nobuo Izumiya et al., "Peptide Gosei no Kiso to Jikken (Base and Experiment for Peptide Synthesis)", 18–19, Maruzen, Tokyo. Described specifically, the target compound can be prepared by reacting the hydrochloride of an amide compound [$H_2N$—$CH(R^1)$—$CONH_2$] with a halogenated formate ester, halogenated phosphate ester or the like in the presence of a base such as amine and then, reacting the resulting product with a base such as potassium hydroxide if necessary.

The compound of the formula (2) can be prepared, for example, by the following process:

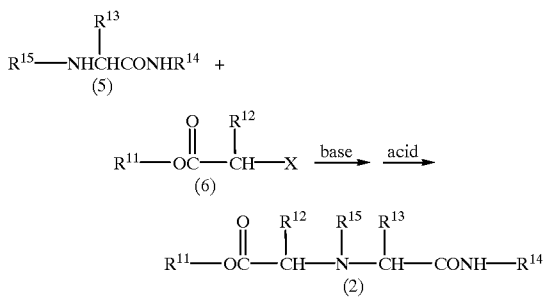

wherein $R^{11}$ to $R^{15}$ have the same meanings as described above and X represents a halogen atom.

A glycinamide derivative (5) is reacted with a halogeno-carboxylic acid derivative (6) in the presence of a base such as sodium hydroxide. The reaction temperature of from −20 to 200° C. and the reaction time of from 10 minutes to 24 hours are preferred. The reaction mixture is then neutralized with an acid such as hydrochloric acid, followed by additional treatments such as drying and isolation if necessary, whereby the compound of the formula (2) can be obtained [see T. Miyazawa, Bull. Chem. Soc. Jpn., 53, 2555(1980)].

The compound of the formula (3) can be prepared, for example, by reacting a dipeptide with a halogenated formate ester in the presence of a base such as amine (see the above-described "Basis and Experiment of Peptide Synthesis").

The compound of the formula (4) can be synthesized, for example, by the process of Nakano et al. [Chem. Lett., 505–8(1990)] as shown by the following reaction scheme:

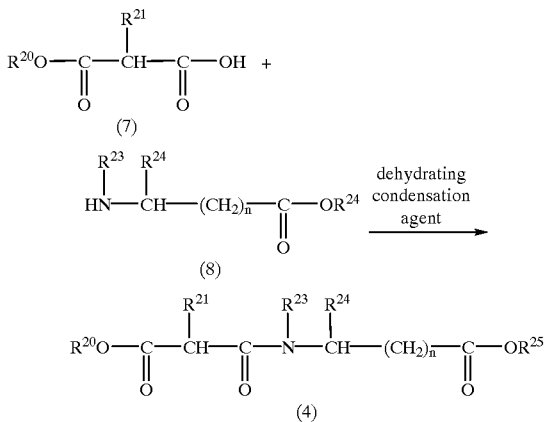

wherein $R^{20}$ to $R^{24}$ and n have the same meanings as described above.

Described specifically, a half ester of malonic acid (7) and an amino acid ester (8) are reacted in the presence of a dehydrating condensation agent. The reaction mixture is reacted with a base such as sodium hydroxide as needed, whereby the target product is obtained. The compound of the formula (4) can also be synthesized by the process of Katsuki et al. [Bull. Chem. Soc. Jpn., 49, 3287–3290(1976)] shown by the following reaction scheme:

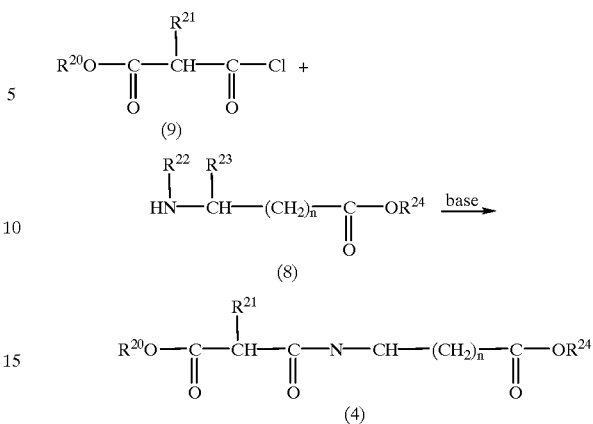

wherein $R^{20}$ to $R^{24}$ and n have the same meanings as described above.

Described specifically, a malonic acid half ester acid chloride (9) is reacted with an amino acid ester (8) in the presence of a base. The reaction mixture is then alkylated by an alkyl halide or hydrolyzed by a base such as sodium hydroxide as needed, whereby the target product is obtained.

Although there is no particular limitation imposed on the amount of any one of the compounds of the formulas (1) to (4) to be incorporated in the skin external preparation of the present invention, an amount of 0.0001 to 40 wt. % based on the whole composition is preferred, with 0.01 to 20 wt. % being particularly preferred.

It is particularly preferred to administer the skin external preparation of the present invention for the purpose of alleviating or preventing skin troubles caused by aging of the skin such as wrinkles, sagging and lowering in resilience, or of inhibiting hair growth.

The present inventors have carried out an investigation on the hair growth inhibitory action of various plant extracts as well as that of the above-described compounds. As a result, it has been found that a plant extract selected from hydrolyzed almond, burnet, clove, rose hips, hawthorn, betula and gambir has excellent hair growth inhibitory action and among them, the hydrolyzed almond extract and clove extract have superior hair growth inhibitory action.

The term "hydrolyzed almond" as used herein means a mixture available by the hydrolysis of seeds (sweet almond) of almond (*Prunus amygdalus Batsch*) belonging to Rosaceae in the presence of an acid or alkali. The term "burnet" means the root and rootstock of burnet (*Sanguisorba of ficinalis L.*) belonging to Rosaceae. The term "clove" means the bud of clove (*Syzygium aromaticum* Merrill et Perry (*Eugenia caryophyllata* Thunberg)) belonging to Myrtaceae. The term "rose hips" means the fruit of a wild rose (*Rosa multiflora* Thunberg) belonging to Rosaceae or a plant analogous thereto. The term "hawthorn" means the terrestrial part of the hawthorn (*Craegus oxyacanth L.*) belonging to Rosaceae. The term "betula" means the leaf, bark and wood parts of European betula (*Betula alba L.*) belonging to Butulaceae. The term "gambir" means the dried solid of a water extract from the leaves and young branches of *Uncaria gambir Roxburgh* belonging to Rubiaceae. These plants have been conventionally used as a herbal and crude drug or food.

The above-described plant extracts, other than the hydrolyzed almond, to be used in the present invention, mean solvent extracts, or diluted solutions, concentrates or dried powders thereof each available by pulverizing the plant, extracting the resulting particles with a solvent at room temperature or under heat or extracting by an extractor such as Soxhlet's extractor.

Examples of the extracting solvent include water, lower alcohols such as ethanol, propanol and butanol, and polyols such as propylene glycol, 1,3-butylene glycol and glycerin and mixtures thereof. Among them, single use of water or a mixture of ethanol or 1,3-butylene glycol and water is preferred, with a 1:1 to 99:1 (volumetric ratio) mixture of ethanol or 1,3-butylene glycol and water being particularly preferred.

The hydrolyzed almond can be obtained, for example, by the following process. Described specifically, it can be obtained by adding 0.1 to 20 v/v % of an acid such as sulfuric acid, hydrochloric acid, acetic acid or phosphoric acid or a 0.01 to 10N alkali such as sodium hydroxide or potassium hydroxide to one or a mixture of at least two of water, methanol, ethanol, propanol, butanol, propylene glycol and 1,3-butylene glycol, preferably water and/or ethanol, immersing silk fibers in the resulting mixture generally at 3 to 100° C. and then removing insoluble matters. This removal of the insoluble matters is preferably conducted after adjusting the pH to about 7.0 with an alkali such as sodium hydroxide, potassium hydroxide, sodium carbonate or sodium bicarbonate or an acid such as sulfuric acid, hydrochloric acid, acetic acid or phosphoric acid in advance.

The above-described extracts can also be used after removal of inert matters therefrom by a technique such as liquid-liquid distribution or removal of a precipitate by adding a solvent. In the present invention, such an extract is preferably employed. The extract may also be used after treatment such as deodorization or decoloring in a known manner as needed.

From the viewpoints of hair growth inhibitory effects, economy and the like, the above-described plant extract is preferably added in an amount of 0.0001 to 50 wt. % as a dry solids content, with 0.001 to 10 wt. % being particularly preferred.

Moreover, it is possible to incorporate a keratinization remedy in the skin external preparation of the present invention, thereby bringing about an improvement in the effects for preventing or alleviating the aging of the skin which appears, for example, as wrinkle formation or for inhibiting hair growth. Examples of the keratinization remedy include sphingosine derivatives.

In addition to the above-described effective ingredient and keratinization remedy, any component can be incorporated in the skin external preparation of the present invention insofar as it does not impair the advantages of the present invention. Examples include purified water, alcohols, chelating agents, various oils, surfactants, emulsifiers, thickening agents, antiseptics, antioxidants, solvents, drug efficacy ingredients, powders, coloring matters and perfumes. It is also possible to incorporate, in the skin external preparation of the present invention, an existing agent for preventing or alleviating skin aging, an existing hair growth inhibitor, an ultraviolet absorber, an ultraviolet protector, collagen, a humectant, an anti-inflammatory, an antioxidant or the like as needed.

The skin external preparation of the present invention can be prepared in various forms in a conventional manner and preferred examples include lotion, emulsion, cream, ointment, stick, solution in an organic solvent, purified water or the like, facial pack and gel. In other words, the skin external preparation of the present invention is used in the form of a lotion, oil essence, O/W type or W/O type cream, emulsion, facial pack, ointment, foundation, skin cleansing agent, tonic or bathing agent.

EXAMPLES

The present invention will hereinafter be described in further detail by examples. It should however be borne in mind that the present invention is not limited to or by the examples.

Synthesis Example 1

Synthesis of N-iso-butoxycarbonyl-L-leucinamide (Compound 1-1)

In a mixed solvent of 150 ml of tetrahydrofuran and 50 ml of distilled water, 5.00 g (30 mmol) of L-leucinamide hydrochloride and 5.46 g (54 mmol) of triethylamine were dissolved, followed by ice cooling to 5° C. Without changing the temperature, 3.29 g (33 mmol) of isobutyl chloroformate was added dropwise to the reaction mixture. After the completion of the dropwise addition, the full consumption of the raw materials was confirmed by thin layer chromatography. To the reaction mixture, 6.53 g (57 mmol) of 85%. phosphoric acid was added to terminate the reaction.

After tetrahydrofuran was distilled off from the reaction mixture under reduced pressure, 300 ml of ethyl acetate was added to the residue to extract the same. The organic layer was washed with distilled water and saturated saline and then dried over anhydrous sodium sulfate. The solvent was then distilled off. The residue was subjected to column chromatography with a mixed solvent of ethyl acetate and n-hexane as an eluent. The solvent was then distilled off, whereby 4.82 g (yield: 80%) of N-iso-butoxycarbonyl-L-leucinamide (Compound 1-1) was obtained. The resulting compound has the following physical properties:

NMR(CDCl$_3$) δ: 0.85(d,3H,J=5H), 0.88(d,3H,J=5Hz), 1.33–1.93(m,4H), 3.73(d,2H,J=7Hz), 3.84–4.00(m,1H), 6.93(s,1H), 7.07(d,1H,J=9Hz), 7.26(s,1H).

Synthesis Example 2

Synthesis of N-carboxy-L-phenylalaninamide potassium salt(Compound 1-2)

In a mixed solvent of 150 ml of tetrahydrofuran and 50 ml of distilled water, 6.00 g (30 mmol) of L-phenylalaninamide hydrochloride and 5.46 g (54 mmol) of triethylamine were dissolved, followed by ice cooling to 5° C. Without changing the temperature, 3.29 g (33 mmol) of isobutyl chloroformate was added dropwise to the reaction mixture. After the completion of the dropwise addition, the full consumption of the raw materials was confirmed by thin layer chromatography. To the reaction mixture, 6.53 g (57 mmol) of 85% phosphoric acid was added to terminate the reaction.

After tetrahydrofuran was distilled off from the reaction mixture under reduced pressure, 300 ml of ethyl acetate was added to the residue to extract the same. The organic layer was washed with distilled water and saturated saline and then dried over anhydrous sodium sulfate. The solvent was then distilled off. The residue was dissolved in 100 ml of ethanol, followed by the addition of a solution of 1.35 g (24 mmol) of potassium hydroxide in 100 ml of distilled water while thorough stirring. After stirring was continued at 70° C. for 3 hours, the reaction was terminated. The solvent was then distilled off and the residue was recrystallized from ethanol—diethyl ether, whereby 5.91 g (yield: 81%) of N-carboxy-L-phenylalaninamide potassium salt(Compound 1-2) was obtained as pale yellow crystals. The resulting compound has the following physical properties:

NMR(DMSO-d$_6$) δ: 2.58(dd,1H,J=8.14Hz), 2.95(dd,1H, J=4.14Hz), 3.45(br.s,2H), 3.70–3.75(m,1H), 6.07(br.s,1H), 7.13–7.28(m,5H)

Synthesis Example 3

Synthesis of N-(dibenzyloxyphosphonyl)-L-leucinamide (Compound 1-3)

In 200 ml of chloroform, 6.0 g (36 mmol) of L-leucinamide hydrochloride and 14.6 g (144 mmol) of triethylamine were dissolved, followed by cooling to 0° C. while through stirring. To the reaction mixture, 16.0 g (54 mmol) of dibenzyl chlorophosphate was added. Without changing the temperature, stirring was continued for 20 hours. After the completion of the reaction, 50 ml of ethanol was added and the resulting mixture was stirred for 30 minutes. The reaction mixture was washed successively with 5% hydrochloric acid, distilled water, a 10% aqueous solution of sodium bicarbonate and saturated saline and then dried over anhydrous sodium sulfate. The solvent was then distilled off under reduced pressure. The residue was subjected to column chromatography with a mixed solvent of chloroform and ethanol as an eluent. After the solvent was distilled off, the residue was recrystallized from ethyl acetate - n-hexane, whereby 9.3 g (yield: 66%) of N-(dibenzyloxyphosphonyl)-L-leucinamide (Compound 1-3) was obtained as white crystals. The resulting compound has the following physical properties:

NMR(CDCl$_3$) δ: 0.84(d,3H,J=4Hz), 0.87(d,3H,J=4Hz), 1.41–1.82(m,3H), 3.70–3.97(m,2H), 4.98(d,2H,J=4Hz), 5.02(d,2H,J=4Hz), 6.93(s,1H), 7.07(d,1H,J=9Hz), 7.26(s, 1H).

Synthesis Example 4

Synthesis of N-phosphono-L-leucinamide dipotassium salt (Compound 1-4)

In 100 ml of methanol, 5.0 g (13 mmol) of N-(dibenzyloxyphoshonyl)-L-leucinamide (Compound 1-3) was dissolved, followed by the addition of 3.3 ml of a 8N aqueous solution of potassium hydroxide and 0.2 g of 10% palladium carbon. The resulting mixture was stirred at room temperature for 2 hours under a hydrogen gas stream. After the completion of the reaction, the reaction mixture was filtered to remove the catalyst and the solvent was distilled off. The residue was recrystallized from ethanol- diethyl ether, whereby 3.2 g (yield: 97%) of N-phosphono-L-leucinamide dipotassium salt (Compound 1-4) was obtained. The resulting compound has the following physical properties:

NMR(D$_2$O) δ: 0.94(d,6H,J=6Hz), 1.47–1.61(m,2H), 1.69–1.79(m,1H), 3.43–3.76(m,1H).

Protons of any amide were not observed at all.

The compounds shown below were each obtained in a similar manner to one of Synthesis Examples 1 to 4.

TABLE 1

| Synthesis Example | Compound | Synthesizing process | Yield % | NMR Solvent | δ |
|---|---|---|---|---|---|
| Synthesis Example 5 | N-carboxy-L-leucinamide potassium salt (Compound 1-5) | Synthesis Example 2 | 82% | DMSO-d$_6$ | 0.87(d, 3H, J=6 Hz), 0.88(d, 3H, J=6 Hz), 0.98–1.81(m, 3H), 3.50–3.72(m, 1H), 5.86(br.s, 2H), 6.65(br.s, 1H) |
| Synthesis Example 6 | N-carboxy-D-leucinamide potassium salt (Compound 1-7) | Synthesis Example 2 | 78% | DMSO-d$_6$ | 0.86(d, 3H, J=6 Hz), 0.88(d, 3H, J=6 Hz), 1.02–1.83(m, 3H), 3.70–3.74(m, 1H), 5.67(s, 1H), 6.23(d, 1H, J=7 Hz), 6.52(s, 1H) |
| Synthesis Example 7 | N-carboxy-L-alaninamide potassium salt (Compound 1-7) | Synthesis Example 2 | 73% | DMSO-d$_6$ | 1.10(d, 3H, J=7 Hz), 3.37–3.42(m, 1H), 6.10(br.s, 1H), 6.26(br.s, 1H), 6.41(br.s, 1H) |
| Synthesis Example 8 | N-carboxy-L-isoleucinamide potassium salt (Compound 1-8) | Synthesis Example 2 | 78% | DMSO-d$_6$ | 0.64(d, 3H, J=7 Hz), 0.77–1.51(m, 6H), 1.57–1.69(m, 1H), 3.41(d, 3H, J=3 Hz), 3.50(d, 3H, J=3 Hz), 6.20(s, 1H) |
| Synthesis Example 9 | N-methoxycarbonyl-L-leucinamide (Compound 1-9) | Synthesis Example 1 | 81% | CDCl$_3$ | 0.88(d, 6H, J=7 Hz), 0.90(d, 6H, J=6 Hz), 1.37–1.92(m, 4H), 3.72(d, 2H, J=6 Hz), 3.87–4.00(m, 1H), 6.92(s, 1H), 7.10(d, 1H, J=10 Hz), 7.23(s, 1H) |
| Synthesis Example 10 | N-(diethoxyphosphonyl)-L-leucinamide (Compound 1-10) | Synthesis Example 3 | 62% | CDCl$_3$ | 0.94(d, 6H, J=6 Hz), 1.30(t, 6H, J=7 Hz), 1.53–1.84(m, 3H), 3.61–3.75(m, 1H), 3.93–4.11(m, 4H), 4.37(t, 1H, J=11 Hz), 6.45(s, 2H), 7.34(s, 1H). |
| Synthesis Example 11 | N-carboxy-L-glycinamide potassium salt (Compound 1-11) | Synthesis Example 2 | 65% | D$_2$O | 3.88(s, 2H) |
| Synthesis Example 12 | N-(phenethyl-phosphonyl)-L-leucinamide (Compound 1-12) | Synthesis Example 3, 4 | 46% | CDCl$_3$ | 0.91(d, 6H, J=6 Hz), 1.37–2.01(m, 5H), 2.76–2.89(m, 2H), 3.58–3.74(m, 1H), 7.13–7.27(m, 7H) The hydroxyl group of the phosphonyl group was not observed at all. |
| Synthesis Example 13 | N-carboxy-L-asparaginamide potassium salt (Compound 1-13) | Synthesis Example 2 | 33% | D$_2$O | 2.67–2.84(m, 2H), 4.40–4.55(m, 1H) |
| Synthesis | N-carboxyl-L- | Synthesis | 37% | DMSO-d$_6$ | 1.51–1.90(m, 2H), 2.00–2.20(m, 1H), |

TABLE 1-continued

| Synthesis Example | Compound | Synthesizing process | Yield % | NMR Solvent | δ |
|---|---|---|---|---|---|
| Example 14 | prolinamide potassium salt (Compound 1-14) | Example 2 | | | 2.70–2.98(m, 1H), 3.40–3.68(m, 2H), 8.31(s, 2H) |

Synthesis Example 15

Synthesis of Compound 2-1

In a flask, 200 ml of water, 20 g of phenylalninamide (0.12 mol), 9.7 g (0.24 mol) of sodium hydroxide and 14 g (0.12 mol) of sodium chloroacetate were charged, followed by heating at 50° C. for 5 hours. After the completion of the reaction, about 7 g of hydrochloric acid was added to the reaction mixture to neutralize the same, followed by drying under reduced pressure, whereby 44 g of a mixture of Compound 2-1 and sodium chloride was obtained. By recrystallization ($H_2O$), Compound 2-1 was isolated (yield: 67%).

NMR(DMSO-$d_6$) δ: 2.75–3.34(4H,m), 3.75(1H,t,J=6.7Hz), 7.27(5H,m), 7.57(1H,s), 7.76(1H,s)

Synthesis Examples 16 to 23

Compounds 2-2 to 2-9 shown in Tables 2 and 3 were synthesized in a similar manner to Synthesis Example 15 by using the amide derivatives shown in Tables 2 and 3.

TABLE 2

| Synthesis Example | Compound | Glycinamide derivative | Halocarboxylic acid derivative | Yield | NMR Solvent | δ |
|---|---|---|---|---|---|---|
| 16 | Compound 2-2 | Phenylalanin-amide | 2-Chloro-propionic acid | 66% | DMSO-$d_6$ | 1.22(3H, d, J=6.9 Hz), 2.25(1H, d, J=3.7 Hz), 3.50–4.45(4H, m), 7.02–7.41(7H, m) |
| 17 | Compound 2-3 | Leucinamide | Sodium chloroacetate | 67% | DMSO-$d_6$ | 0.82–1.02(6H, m), 1.54(2H, t, J=6.6 Hz), 1.46–1.80(1H, m), 3.04–3.60(3H, m), 3.56(1H, t, J=7.1 Hz), 7.50(1H, s), 7.86(1H, s) |
| 18 | Compound 2-4 | Glutamic acid diamide | Chloroacetic acid | 48% | DMSO-$d_6$ | 1.61–2.00(2H, s), 2.00–2.38(4H, m), 2.99–3.30(1H, m), 6.81(1H, d, J=15.6 Hz), 7.29(1H, d, J=30.0 Hz), 7.41(1H, d, J=15.6 Hz), 7.69(1H, d, J=31.4 Hz) |
| 19 | Compound 2-5 | Glutamic acid diamide | 2-Chloro-propionic acid | 68% | DMSO-$d_6$ | 1.16(3H, d, J=6.8 Hz), 1.25–1.41(2H, m), 1.64–2.00(2H, m), 2.00–2.36(2H, m), 7.0–7.86(4H, m) |

TABLE 3

| Synthesis Example | Compound | Glycinamide derivative | Halocarboxylic acid derivative | Yield | NMR Solvent | δ |
|---|---|---|---|---|---|---|
| 20 | Compound 2-6 | Asparatic acid diamide | Chloroacetic acid | 41% | DMSO-$d_6$ | 2.92(2H, d, J=5.12 Hz), 3.20–4.22(2H, m), 4.27(1H, m), 5.02–7.35(4H, m) |
| 21 | Compound 2-7 | Asparatic acid diamide | 1-Chloro-propionic acid | 40% | DMSO-$d_6$ | 1.21(3H, d, J=6.92 Hz), 3.23–4.71(4H, m), 6.98–7.17(2H, m), 7.59–7.79(2H, m) |
| 22 | Compound 2-8 | Prolinamide | Chloroacetic acid | 52% | DMSO-$d_6$ | 1.50–1.88(4H, m), 7.11(1H, s), 1.90–2.22(1H, m), 7.38(1H, s), 2.40–2.60(1H, m), 2.97–3.33(1H, m), 3.27(2H, dd, J=44.9, 17.1 Hz) |
| 23 | Compound 2-9 | Prolinamide | 1-Chloro-propionic acid | 26% | DMSO-$d_6$ | 1.01–1.32(7H, m), 7.14(1H, s), 1.50–1.86(2H, m), 7.31(1H, s), 2.61–2.83(1H, m), 4.01(1H, q, J=6.9 Hz) |

Synthesis Example 24

Synthesis of Compound 3-1

In 50 ml of chloroform, 1.00 g (3.9 mmol) of L-leucyl-L-leucine methyl ester and 0.78 g (7.8 mmol) of triethylamine were dissolved, followed by ice cooling to 5° C. Without changing the temperature, 0.59 g (4.3 mmol) of isobutyl chloroformate was added dropwise. After the completion of the dropwise addition, the full consumption of the raw materials was confirmed by thin-layer chromatography. To the reaction mixture, 0.49 g (4.3 mmol) of 85% phosphoric acid was added to terminate the reaction. The organic layer was washed with distilled water and saturated saline and then dried over anhydrous sodium sulfate. The solvent was distilled off and the residue was subjected to column chromatography with an ethyl acetate -n-hexane mixed solvent as an eluent. The solvent was then distilled off, whereby 0.91 g (yield: 65%) of Compound 3-1 was obtained.

NMR(DMSO-$d_6$) δ: 0.83–0.90(m,18H), 1.01–1.93(m, 7H), 3.61(s,3H), 3.73(d,2H,J=7Hz), 4.00–4.12(m,1H), 4.24–4.30(m,1H), 7.09(d,1H,J=8Hz), 8.12(d,1H,J=8Hz).

Synthesis Example 25

Synthesis of Compound 3-2

In a mixed solvent of 20 ml of tetrahydrofuran and 10 ml of distilled water, 1.00 g (4.1 mmol) of L-isoleucyl-L-isoleucine and 0.83 g (8.2 mmol) of triethylamine were dissolved, followed by ice cooling to 5° C. Without changing the temperature, 0.43 g (4.5 mmol) of methyl chloroformate was added dropwise. After the completion of the dropwise addition, the full consumption of the raw materials was confirmed by thin-layer chromatography. To the reaction mixture, 0.98 g (8.2 mmol) of 85% phosphoric acid was added to terminate the reaction.

Tetrahydrofuran was distilled off from the reaction mixture under reduced pressure. To the residue, 100 ml of ethyl acetate was added to extract the same. The organic layer was washed with distilled water and saturated saline and then dried over anhydrous sodium sulfate. The solvent was distilled off and the residue was dissolved in 20 ml of ethanol. While thorough stirring, a solution of 0.46 g (8.2 mmol) of potassium hydroxide in 20 ml of distilled water was added to the resulting solution, followed by stirring at 70° C. for 3 hours. After the full consumption of the raw materials was confirmed by thin layer chromatography, 0.80 g (82 mmol) of 85% phosphoric acid was added to terminate the reaction. To the reaction mixture, 300 ml of ethyl acetate was added to extract the same. The organic layer was washed with distilled water and saturated saline and then dried over anhydrous sodium sulfate. The solvent was distilled off and the residue was recrystallized from ethyl acetate - n-hexane, whereby 0.60 g (yield: 51%) of Compound 3-2 was obtained as white crystals.

NMR(DMSO-$d_6$) δ: 0.77–0.90(m,12H), 1.02–1.46(m, 4H), 1.66–1.86(m,2H), 4.01–4.14(m,1H), 4.20–4.27(m,1H), 6.31(d,1H,J=9Hz), 6.41(d,1H,J=9Hz), 12.47(br.s,2H).

Synthesis Examples 26 to 28

Compounds 3-3 to 3-5 were synthesized in a similar manner to Synthesis Example 25 by using the dipeptide and chloroformate ester shown in Table 4.

TABLE 4

| Synthesis Example | Compound | Dipeptide | Chloroformate ester | Yield | NMR Solvent | δ |
|---|---|---|---|---|---|---|
| 26 | Compound 3-3 | L-phenyl-alanyl-L-phenylalanine methyl ester | Methyl chloroformate | 55% | DMSO-$d_6$ | 2.62–3.12(m, 4H), 3.45(s, 3H), 3.60(s, 3H), 4.20–4.31(m, 1H), 4.47–4.58(m, 1H), 7.17–7.30(m, 11H), 8.43(d, 1H, J=8 Hz) |
| 27 | Compound 3-4 | L-leucyl-glycine methyl ester | Methyl chloroformate | 61% | DMSO-$d_6$ | 0.87(d, 6H, J=7 Hz), 1.40–1.47(m, 2H), 1.51–1.72(m, 1H), 3.33(s, 3H), 3.61(s, 3H), 3.83–3.63(m, 2H), 3.89–4.10(m, 1H), 7.11(d, 1H, J=8 Hz), 8.22(t, 1H, J=6 Hz) |
| 28 | Compound 3-5 | L-phenyl-alanyl-glycine | Methyl chloroformate | 49% | DMSO-$d_6$ | 2.79–3.04(m, 2H), 3.67(d, 2H, J=6 Hz), 4.28–4.38(m, 1H), 6.33–6.40(m, 2H), 7.15–7.30(m, 5H), 12.48(bs, 1H) |

Synthesis Example 29

Synthesis of Compound 4-1

In 50 ml of chloroform, 16.05 g (114 mmol) of glycine ethyl ester hydrochloride and 23.27 g (228 mmol) of triethylamine were dissolved, followed by ice cooling to 5° C. Without changing the temperature, 10.00 g (57 mmol) of ethylmalonyl chloride was added dropwise to the resulting solution. After the completion of the dropwise addition, the full consumption of the raw materials was confirmed by thin layer chromatography. To the reaction mixture, a 5% aqueous phosphoric acid solution was added to terminate the reaction. The organic layer was washed with distilled water and saturated saline and then dried over anhydrous sodium sulfate. The solvent was distilled off. The residue was subjected to column chromatography with a mixed solvent of ethyl acetate and n-hexane as an eluent. The solvent was distilled off, whereby 9.40 g (yield: 76%) of Compound 4-1 was obtained.

NMR(DMSO-$d_6$) δ: 2.48–2.51(m,6H), 3.30(d,2H,J=9Hz), 3.85(d,2H,J=6Hz), 4.02–4.20(m,4H), 8.49(t,1H,J=5Hz).

Synthesis Example 30

Synthesis of Compound 4-2

In 50 ml of dehydrated tetrahydrofuran, 5.00 g (23.0 mmol) of Compound 4-1 was dissolved. The resulting solution was added to a suspension of 1.10 g (27.6 mmol) of sodium hydride in 30 ml of tetrahydrofuran, followed by heating to 50° C. After the slow dropwise addition of 3.74 g (21.9 mmol) of benzyl bromide and stirring for three hours at the same temperature, the reaction was terminated. After cooling, a 5% aqueous solution of phosphoric acid was added to the reaction mixture, followed by extraction with 300 ml of ethyl acetate. The organic layer was washed with a saturated aqueous solution of sodium bicarbonate and saturated saline and then dried over anhydrous sodium sulfate. The solvent was distilled off and the residue was subjected to chromatography with a mixed solvent of ethyl acetate and n-hexane as an eluent. By distilling off the solvent, 3.89 g (yield: 55%) of Compound 4-2 was obtained. NMR(DMSO-$d_6$) δ: 1.16(t,1H,J=7Hz), 2.93–3.19(m,2H), 3.71(t,1H,J=7Hz), 3.80(d,2H,J=6Hz), 4.06(q,4H,J=7Hz), 7.13–7.29(m,5H), 8.61(t,1H,J=6Hz).

Synthesis Example 31

Synthesis of Compound 4-3

In 30 ml of methanol, 3.00 g (9.8 mmol) of Compound 4-2 was dissolved. To the resulting solution, a solution of 1.20 g (21.5 mmol) of potassium hydride in 10 ml of water was added. After the resulting mixture was stirred at room temperature for 2 hours, the reaction was terminated. Methanol was distilled off under reduced pressure. To the residue, a 5% aqueous solution of phosphoric acid was added and the resulting crystals were collected by filtration. The crystals were washed with water and then dried under reduced pressure, whereby 2.17 g (yield: 88%) of Compound 4-3 was obtained.

NMR(DMSO-$d_6$) δ: 2.90(m,2H), 3.59(t,1H,J=7Hz), 3.74(d,2H,J=6Hz), 7.12–7.32(m,5H), 8.37(t,1H,J=6Hz), 12.49(br.s,2H)

Synthesis Examples 32 to 34

Compounds 4-4 to 4-6 were synthesized in similar manners to Synthesis Examples 29 to 31 by using the amino acid ester and alkyl halide shown in Table 5.

TABLE 5

| Synthesis Example | Synthesizing process | Amino acid ester | Alkyl halide | Yield | NMR | |
|---|---|---|---|---|---|---|
| 32 | 30 | — | Bromo-biphenyl-methane | 61% | DMSO-$d_6$ | 1.14–1.25(m, 6H), 2.99–3.20(m, 2H), 3.77(t, 1H, J=8 Hz), 3.87(d, 2H, J=8 Hz), 3.98–4.19(m, 4H), 7.24–7.65(m, 9H), 8.63(t, 1H, J=5 Hz) |
| 33 | 29 30 31 | β-alanine methyl ester hydrochloride | Benzyl-bromide | 55% | DMSO-$d_6$ | 2.15–2.39(m, 2H), 2.90–3.09(m, 2H), 3.10–3.34(m, 2H), 3.54(t, 1H, J=8 Hz), 7.00–7.35(m, 5H), 8.11(t, 1H, J=5 Hz), 12.38(br.s, 2H) |
| 34 | 29 31 | L-phenylalanine methyl ester hydrochloride | — | 68% | DMSO-$d_6$ | 2.84–3.10(m, 2H), 3.17(s, 2H), 4.42–4.53(m, 1H), 7.09–7.35(m, 5H), 8.35(d, 1H, J=8 Hz), 12.24(br.s, 2H) |

Test 1: Wrinkle formation inhibition in a hairless rat

The back side of a hairless mouse (HR/ICR, 6 week age at the start of the test) was exposed to UV-B light by a health light lamp ("SE20", trade name; product of Toshiba Electric) at a dose adjusted to 1 MED or less/once. Immediately after the exposure, 100 μl of an 80% ethanol solution (test substance) containing the test compound was applied. The above procedure was carried out for 20 weeks. The energy amount was measured by a UV radiometer ("UVR-305/365D; manufactured by Tokyo Optical Co.). For a control group, only 80% ethanol was applied and tested in the same way. After the test, the degree of wrinkles were evaluated visually by the following criterion (wrinkle index). The results are shown in Table 6.

<Wrinkle degree>

0: No wrinkle was formed.

1: A few shallow wrinkles were formed.

2: A slight amount of wrinkles was formed.

3: Some wrinkles were formed.

4: Deep wrinkles were formed.

TABLE 6

| Test substance | Concentration of application | Wrinkle index | Test substance | Concentration of application | Wrinkle index |
|---|---|---|---|---|---|
| Control | — | 3.06 ± 0.13 | Compound 2-1 | 1 mM | 1.13 ± 0.11 |
| Compound 1-1 | 10 mM | 2.05 ± 0.09 | Compound 2-2 | 1 mM | 1.62 ± 0.10 |
| Compound 1-2 | 1 mM | 1.93 ± 0.12 | Compound 2-3 | 1 mM | 2.08 ± 0.10 |
| Compound 1-3 | 10 mM | 2.91 ± 0.06 | Compound 2-4 | 10 mM | 2.88 ± 0.14 |
| Compound 1-4 | 1 mM | 1.62 ± 0.10 | Compound 2-5 | 10 mM | 1.98 ± 0.17 |
| Compound 1-5 | 1 mM | 1.69 ± 0.15 | Compound 2-6 | 10 mM | 2.48 ± 0.21 |
| Compound 1-6 | 10 mM | 2.63 ± 0.05 | Compound 2-7 | 10 mM | 2.56 ± 0.15 |
| Compound 1-7 | 10 mM | 2.88 ± 0.11 | Compound 2-8 | 10 mM | 1.69 ± 0.15 |
| Compound 1-8 | 1 mM | 1.81 ± 0.06 | Compound 2-9 | 10 mM | 1.93 ± 0.12 |
| Compound 1-9 | 1 mM | 2.21 ± 0.15 | Compound 3-1 | 10 mM | 1.69 ± 0.15 |
| Compound 1-10 | 10 mM | 2.68 ± 0.09 | Compound 3-2 | 1 mM | 1.93 ± 0.12 |
| Compound 1-11 | 20 mM | 2.83 ± 0.10 | Compound 3-3 | 10 mM | 2.88 ± 0.11 |
| Compound 1-12 | 1 mM | 1.68 ± 0.14 | Compound 3-4 | 1 mM | 1.62 ± 0.10 |
| Compound 1-13 | 1 mM | 1.87 ± 0.12 | Compound 3-5 | 10 mM | 2.43 ± 0.16 |
| Compound 1-14 | 1 mM | 1.71 ± 0.08 | Compound 4-1 | 10 mM | 2.42 ± 0.15 |
|  |  |  | Compound 4-2 | 1 mM | 1.25 ± 0.12 |
|  |  |  | Compound 4-3 | 0.1 mM | 2.01 ± 0.21 |
|  |  |  | Compound 4-4 | 0.1 mM | 1.81 ± 0.14 |
|  |  |  | Compound 4-5 | 0.1 mM | 1.44 ± 2.91 |
|  |  |  | Compound 4-6 | 1 mM | 1.83 ± 0.09 |

From the results of Table 6, it has been found that Compounds of the formulas (1) to (4) had marked wrinkle formation inhibitory action and showed excellent effects for preventing or alleviating aging of the skin.

Test 2: Maintenance of skin elasticity in a rat

The bottoms of the both hind feet of three-week old SD male rats were classified into 4 groups, that is, a test-substance (as a 80% ethanol solution) applied group, a solvent (80% ethanol) applied group and an untreated group. After exposure to UV-B light (1 MED or less), the test substance or solvent was applied in an amount of 10 μl/foot. The above procedure was carried out on alternate days, three times a week for six weeks.

The elasticity of the skin was determined by measuring the displacement for 3 seconds after sucking of the skin was started at 500 mb and 3 seconds after sucking was stopped, totally for 6 seconds, by using a cutometer "SES575" (trade name, product of Courage Kazaka). The measurement was carried out five times/foot, whereby Ue and Uf values were found.

The linearity of elastic fibers was analyzed in accordance with the method of Imokawa et al. [J. Invest. Dermatol., 105, 254–258(1995)] using image analysis of a SEM micrograph. Described specifically, samples for scanning electron microscope (SEM) were prepared by fixing the bottom of a leg of a rat under reflux with Mercox (Dainippon Ink & Chemicals, Inc.), followed by digestion with formic acid. From SEM micrographs (×1000) of each of the samples, typical ten micrographs were selected and their enlarged copies were formed. The enlarged micrographs were each divided into 16 regions uniformly. From each of the regions, any one of the elastic fibers was selected and traced on a clear film with a line of a fixed width (8 pixel width). Provided that an area surrounded by the line tracing the elastic fiber is A and the longitudinal length and lateral length of the minimum rectangle surrounding the trace are B and C, respectively, the linearity of the elastic fiber is represented by A/(B×C). For example, if the trace of the elastic fiber is linear, the linearity becomes 1. The results are shown in Table 7.

TABLE 7

| Tested substance | Evaluated concentration | Ue value | Uf value | Linearity |
|---|---|---|---|---|
| Untreated group | — | 0.03294 ± 0.01531* | 0.04833 ± 0.01700* | 0.7345 ± 0.0333* |
| Solvent applied group | — | 0.02125 ± 0.00875## | 0.03333 ± 0.01111## | 0.5133 ± 0.0600## |
| Compound 1-5 | 0.2 wt. % | 0.03269 ± 0.01313* | 0.04800 ± 0.01833* | 0.7330 ± 0.0367* |
| Compound 1-12 | 0.3 wt. % | 0.02969 ± 0.01344* | 0.04311 ± 0.01678*# | 0.7067 ± 0.0653* |
| Compound 2-1 | 0.2 wt. % | 0.03269 ± 0.01313* | 0.04800 ± 0.01833* | 0.7330 ± 0.0367* |
| Compound 2-2 | 0.3 wt. % | 0.02969 ± 0.01344* | 0.04311 ± 0.01678*# | 0.7067 ± 0.0653* |
| Compound 3-2 | 0.2 wt. % | 0.03269 ± 0.01313* | 0.04800 ± 0.01833* | 0.7330 ± 0.0367* |
| Compound 3-4 | 0.3 wt. % | 0.02969 ± 0.01344* | 0.04311 ± 0.01678*# | 0.7067 ± 0.0653* |
| Compound 4-2 | 0.1 wt. % | 0.02341 ± 0.01344* | 0.04711 ± 0.02133* | 0.7221 ± 0.0299* |
| Compound 4-3 | 0.1 wt. % | 0.03359 ± 0.01131* | 0.04323 ± 0.01722* | 0.7013 ± 0.0655* |

*: $p < 0.005$ (vs the solvent applied group)
: $p < 0.005$ (vs the untreated group)
: $p < 0.005$ (vs the untreated group)

From the results of Table 7, it has been found that the compounds of the formulas (1) to (4) showed effects for strongly preventing the lowering of the skin elasticity caused by UV-B and the deterioration of the three-dimensional structure of the elastic fibers which will be a cause for the lowering, thereby maintaining the flexibility of the skin.

Test 3: Hair growth inhibition in a mouse

The 2×4 $cm^2$ portion of the back of each of 6-week old $C_3H$ mice employed in groups, each consisting of five mice, was shaved by an electric clippers and electric shaver with a care so as not to injure the skin. To the shaved portion, a sample was applied in an amount of 100 μl twice a day for 4 weeks. The test substance was dissolved in a solvent (80% ethanol) to adjust its concentration as shown in Table 7. To the control group, only the solvent was applied. After three weeks, in order to observe the hair regrowth, the shaved portion was photographed at a certain magnification and by using an image analyzer, the area ratio of the regrown hair (area of regrown hair/shaved area) was compared with that of the control group. The hair growth inhibition ratio was indicated as a relative value (%) provided that the area ratio of the regrown hair of the control group was 100. The results are shown in Tables 8 and 9.

-continued

|  | (wt. %) |
|---|---|
| Cetanol | 4.0 |
| Squalane | 8.0 |
| Vaseline | 5.0 |
| Hydrogenated palm oil | 4.0 |
| Polyoxyethylene sorbitan monostearate (20.E.O.) | 1.4 |
| Lipophilic glycerin monostearate | 2.4 |
| Butyl paraben | 0.1 |
| Glycerin | 3.0 |
| L-arginine 10.0 wt. % potassium hydroxide | 0.2 |

TABLE 8

| Tested substance | Concentration of application | Hair growth inhibition 3 weeks after shaving | Test substance | Concentration of application | Hair growth inhibition 3 weeks after shaving |
|---|---|---|---|---|---|
| Compound 1-1 | 1 mM | 65.3% | Compound 2-1 | 1 mM | 72.2% |
| Compound 1-2 | 1 mM | 52.6% | Compound 2-2 | 1 mM | 60.3% |
| Compound 1-3 | 10 mM | 72.2% | Compound 2-3 | 1 mM | 70.4% |
| Compound 1-4 | 1 mM | 60.3% | Compound 2-4 | 10 mM | 42.3% |
| Compound 1-5 | 1 mM | 54.6% | Compound 2-5 | 10 mM | 32.8% |
| Compound 1-6 | 10 mM | 53.8% | Compound 2-6 | 10 mM | 48.9% |
| Compound 1-7 | 10 mM | 52.1% | Compound 2-7 | 10 mM | 33.5% |
| Compound 1-8 | 1 mM | 60.5% | Compound 2-8 | 10 mM | 52.1% |
| Compound 1-9 | 1 mM | 64.9% | Compound 2-9 | 10 mM | 52.6% |
| Compound 1-10 | 1 mM | 73.1% | Compound 3-1 | 1 mM | 65.3% |
| Compound 1-11 | 20 mM | 51.0% | Compound 3-2 | 1 mM | 52.6% |
| Compound 1-12 | 1 mM | 71.3% | Compound 3-3 | 10 mM | 72.2% |
| Compound 1-13 | 1 mM | 69.5% | Compound 3-4 | 1 mM | 60.3% |
| Compound 1-14 | 1 mM | 70.6% | Compound 3-5 | 10 mM | 56.6% |
|  |  |  | Compound 4-1 | 10 mM | 49.3% |
|  |  |  | Compound 4-2 | 0.1 mM | 83.4% |
|  |  |  | Compound 4-3 | 0.1 mM | 75.3% |
|  |  |  | Compound 4-4 | 0.1 mM | 84.3% |
|  |  |  | Compound 4-5 | 0.1 mM | 72.6% |
|  |  |  | Compound 4-6 | 1 mM | 48.3% |

TABLE 9

| Tested substance | Concentration | Hair growth inhibition 3 weeks after shaving |
|---|---|---|
| Hydrolyzed almond (5% H$_2$SO$_4$) extract | 1% (solid content) | 82.5% |
| Water extract of burnet | 0.20% (solid content) | 43% |
| Ethanol extract of clove | 0.20% (solid content) | 66.3% |
| Water extract of rose hips | 0.20% (solid content) | 54.7% |
| 50% Ethanol extract of hawthorn | 1% (solid content) | 42.3% |
| 50% Ethanol extract of betula | 1% (solid content) | 31.3% |
| Ethanol extract of gambir | 0.20% (solid content) | 35.6% |

From the results of Tables 8 and 9, it has been found that the compounds of the formulas (1) to (4) had excellent hair growth inhibitory effects.

Formulation Example 1

According to the formulation as described below, a cream for alleviating skin aging was prepared in a conventional manner.

|  | (wt. %) |
|---|---|
| Compound (1-5), (2-1), (3-5) or (4-3) | 0.2 |
| Stearic acid | 2.0 |

-continued

|  | (wt. %) |
|---|---|
| Perfume | 0.1 |
| Purified water | Balance |
| Total | 100.0 |

Formulation Example 2

According to the formulation as described below, a facial pack for preventing or alleviating skin aging was prepared in a conventional manner.

|  | (wt. %) |
| --- | --- |
| Compound (1-5), (2-1), (3-5) or (4-3) | 3.0 |
| Polyvinyl alcohol | 20.0 |
| Glycerin | 5.0 |
| Ethanol | 16.0 |
| Perfume | 0.1 |
| Coloring matter | 0.1 |
| Purified water | Balance |
| Total | 100.0 |

Formulation Example 3

According to the formulation as described below, a hair growth inhibiting lotion was prepared. Described specifically, a solution of components belonging to A was prepared, while another solution of components belonging to B was prepared. To the solution A, the solution B was added and they were mixed by uniform stirring, whereby a hair growth inhibiting lotion was prepared.

|  |  | (wt. %) |
| --- | --- | --- |
| A: | Polyoxyethylene hydrogenated castor oil | 0.8 |
|  | Ethanol | 30.0 |
| B: | Compound (1-5), (2-1), (3-5) or (4-3) | 1.0 |
|  | Sodium dodecyl sulfate | 0.12 |
|  | Dodecyl methylamine oxide | 0.18 |
|  | Isopropyl alcohol | 15.0 |
|  | Benzyl alcohol | 12.0 |
|  | Glycerin | 2.0 |
|  | Purified water | Balance |
| Total |  | 100.0 |

Formulation Example 4

According to the formulation as described below, a hair growth inhibiting aerosol was prepared. Described specifically, components belonging to A were uniformly mixed and charged in a container. The container was then filled with B in a conventional manner, whereby the hair growth inhibiting aerosol was prepared.

|  |  | (wt. %) |
| --- | --- | --- |
| A: | Compound (1-5), (2-1), (3-5) or (4-3) | 1.0 |
|  | Cetanol | 1.2 |
|  | Propylene glycol | 4.0 |
|  | Ethanol | 8.0 |
|  | Purified water | Balance |
| B: | Liquefied petroleum gas (propellant) | 4.0 |
| Total |  | 100.0 |

Japanese Patent Application No. 10-081418 filed on Mar. 27, 1998, is incorporated herein by reference in its entirety.

What is claimed is:

1. A method of inhibiting hair growth which comprises applying to the body of a subject a composition comprising, as an effective ingredient, a plant extract selected from the group consisting of hydrolyzed almond, burnet, clove, rose hips, hawthorn, betula and gambir.

2. The method according to claim 1, wherein the extract is present in an amount ranging from 0.0001 to 50 wt. %.

3. The method according to claim 1 wherein the extract is present in an amount ranging from 0.001 to 10 wt. %.

4. The method according to claim 1 wherein the composition is in the form of a lotion, cream, emulsion, ointment, stick, solution, facial pack, aerosol or gel.

* * * * *

UNITED STATES PATENT AND TRADEMARK OFFICE
Certificate

Patent No. 6,171,595 B1                                                     Patented: January 9, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: David Grant Midkiff, Alpharetta, GA; and John Joseph Lassig, Cumming, GA.

Signed and Sealed this Twenty-Ninth Day of October 2002.

*DAVID A. SIMMONS*
*Supervisory Patent Examiner*
Art Unit 1724